United States Patent [19]
Jolly et al.

[11] Patent Number: 5,827,309
[45] Date of Patent: Oct. 27, 1998

[54] GUARDED SURGICAL SCALPEL WITH SCALPEL BLADE REMOVER

[75] Inventors: Neil Jolly, Brighton, Mass.; Craig D. Newman, New York, N.Y.; Robert W. Pierce, Wrentham, Mass.

[73] Assignee: Becton, Dickinson and Company, Franklin Lakes, N.J.

[21] Appl. No.: 545,488

[22] Filed: Oct. 19, 1995

Related U.S. Application Data

[63] Continuation-in-part of Ser. No. 379,245, Jan. 27, 1995, Pat. No. 5,752,968, Continuation-in-part of Ser. No. 328,996, Oct. 25, 1994, Pat. No. 5,620,454.

[51] Int. Cl.$^6$ ............................. A61B 17/32; A61B 19/00
[52] U.S. Cl. ............................................. 606/167; 128/898
[58] Field of Search ................................. 606/1, 167–171, 606/174, 184, 185, 181; 30/2, 151, 158, 167, 335, 339

[56] References Cited

U.S. PATENT DOCUMENTS

| | | |
|---|---|---|
| 1,914,153 | 6/1933 | Ogden . |
| 2,039,443 | 5/1936 | Ogden .............................................. 30/9 |
| 2,885,780 | 5/1959 | Campbell . |
| 3,706,106 | 12/1972 | Leopoldi . |
| 3,905,101 | 9/1975 | Shepard ..................................... 30/162 |
| 3,906,626 | 9/1975 | Riuli ......................................... 30/162 |
| 3,943,627 | 3/1976 | Stanley, Jr. ................................. 30/151 |
| 4,091,537 | 5/1978 | Stevenson, Jr. ............................. 30/286 |
| 4,393,587 | 7/1983 | Kloosterman .............................. 30/162 |
| 4,414,974 | 11/1983 | Dotson et al. . |
| 4,491,132 | 1/1985 | Aikins . |
| 4,516,575 | 5/1985 | Gerhard et al. . |
| 4,523,379 | 6/1985 | Osterhout et al. ......................... 30/151 |
| 4,576,164 | 3/1986 | Richeson . |
| 4,719,915 | 1/1988 | Porat et al. . |
| 4,735,202 | 4/1988 | Williams . |
| 4,757,612 | 7/1988 | Peyrot ....................................... 30/151 |
| 4,790,312 | 12/1988 | Capuano, Sr. et al. . |
| 4,985,034 | 1/1991 | Lipton ..................................... 606/167 |
| 5,071,426 | 12/1991 | Dolgin et al. ............................ 606/167 |
| 5,139,507 | 8/1992 | Dolgin et al. ............................ 606/167 |
| 5,141,517 | 8/1992 | Shutt ........................................ 606/167 |
| 5,201,748 | 4/1993 | Newman et al. ......................... 606/167 |
| 5,207,696 | 5/1993 | Matwijcow .............................. 606/167 |
| 5,250,063 | 10/1993 | Abidin et al. ............................ 606/167 |
| 5,258,001 | 11/1993 | Corman ................................... 606/167 |
| 5,275,606 | 1/1994 | Abidin et al. ............................ 606/167 |
| 5,292,329 | 3/1994 | Werner .................................... 606/167 |
| 5,292,330 | 3/1994 | Shutt ........................................ 606/170 |
| 5,299,357 | 4/1994 | Wonderley et al. ........................ 30/339 |
| 5,309,641 | 5/1994 | Wonderley et al. ........................ 30/339 |
| 5,312,429 | 5/1994 | Noack ...................................... 606/167 |

(List continued on next page.)

FOREIGN PATENT DOCUMENTS

| | | |
|---|---|---|
| 1 134 793 | 8/1962 | Germany . |
| 3722899 | 1/1989 | Germany . |
| 4 040 909 | 6/1992 | Germany . |
| 91/03984 | 4/1991 | WIPO . |

*Primary Examiner*—Glenn Dawson
*Attorney, Agent, or Firm*—Arthur D. Dawson

[57] ABSTRACT

This invention relates to an improved guarded surgical scalpel having a movable guard that can be retracted to expose the blade and that can be extended to cover the sharp cutting edge of the blade. The guard is telescopically mounted inside the blade handle and includes a deflectable top wall portion that holds a detent pin or that defines a radially extending flange. This detent pin or flange engages a slot having upturned ends formed in at least one side wall of the blade handle. The detent pin or flange is biased upwardly into the upturned ends of the slot to hold the guard in the retracted or extended position. The blade can include a tang having a notch formed therein. The distal end of one sidewall of the guard can be formed with a complementary notch such that when the distal end of the sidewall of the guard engages the proximal end of the blade, forward movement of the guard forces the blade off of the scalpel. A lifter wedge is provided to urge the proximal end of the blade away from a blade carrier into engagement with the distal end of the sidewall of the guard.

14 Claims, 10 Drawing Sheets

U.S. PATENT DOCUMENTS

| | | | |
|---|---|---|---|
| 5,330,492 | 7/1994 | Haugen | 606/167 |
| 5,330,493 | 7/1994 | Haining | 606/167 |
| 5,330,494 | 7/1994 | Van Der Westhuizen et al. | 606/167 |
| 5,336,176 | 8/1994 | Yoon | 604/51 |
| 5,342,379 | 8/1994 | Volinsky | 606/167 |
| 5,344,424 | 9/1994 | Roberts et al. | 606/167 |
| 5,411,512 | 5/1995 | Abidin et al. | 606/167 |
| 5,417,704 | 5/1995 | Wonderley | 606/167 |
| 5,423,843 | 6/1995 | Werner | 606/167 |
| 5,430,942 | 7/1995 | Doucette | 606/167 |
| 5,496,340 | 3/1996 | Abidin et al. | 606/167 |

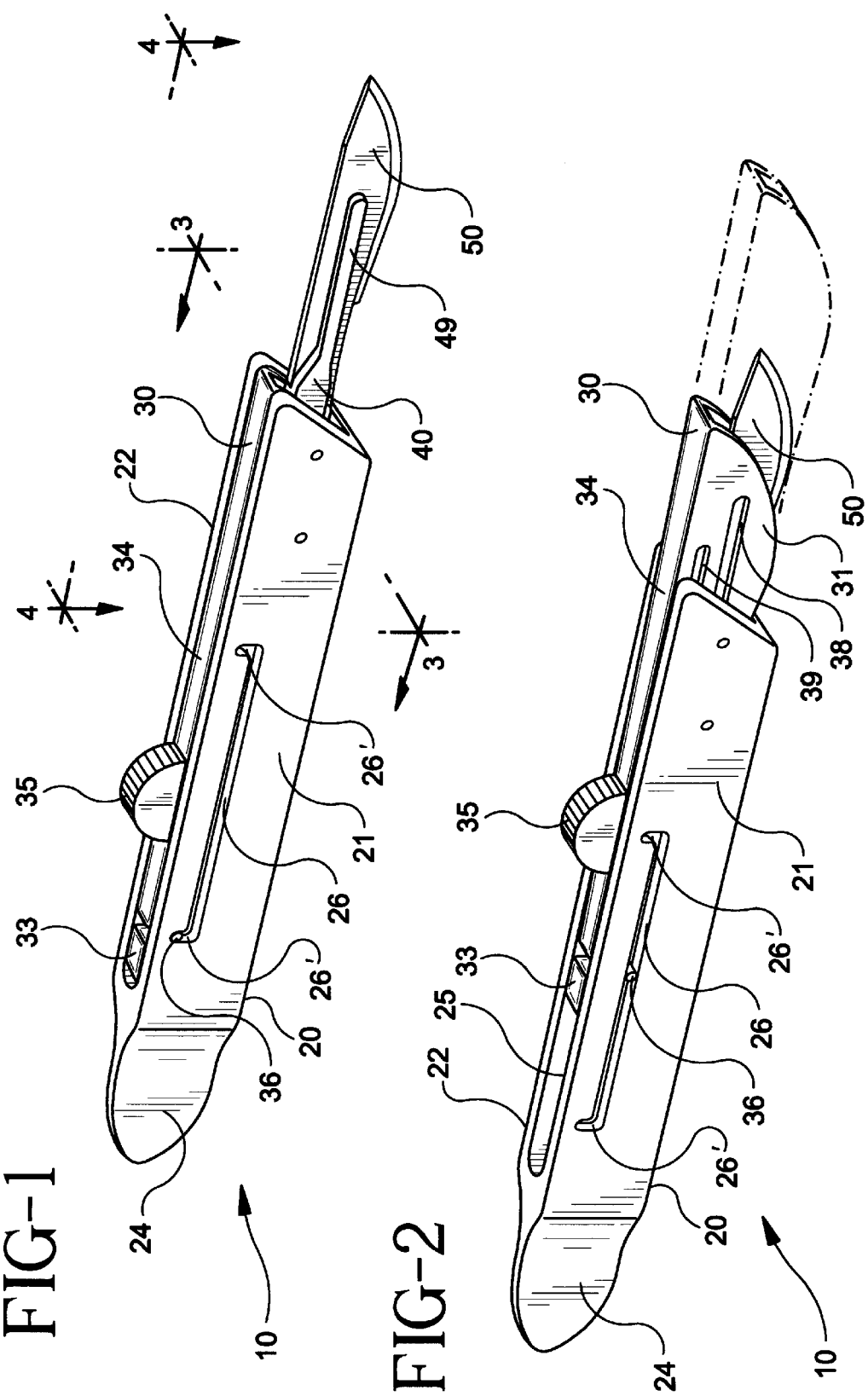

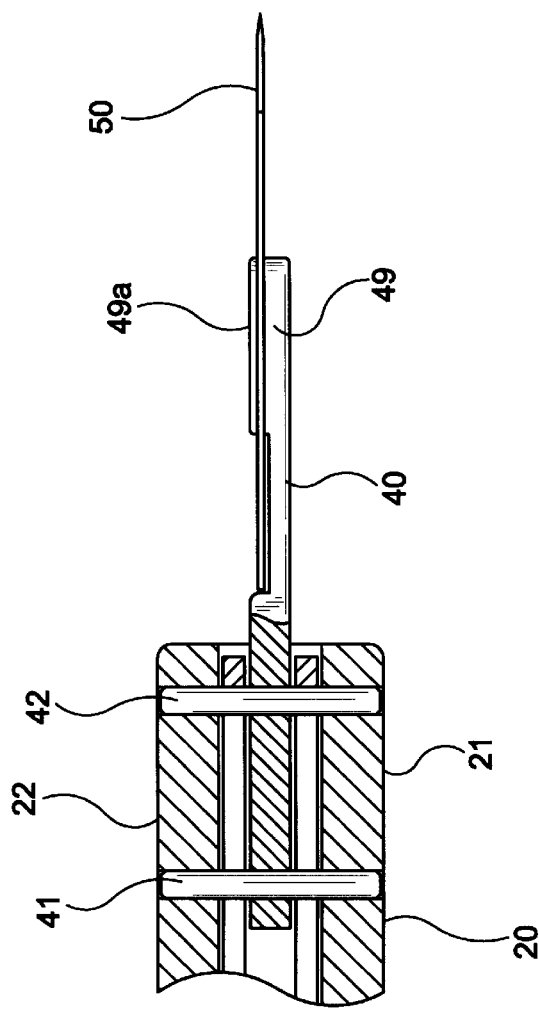
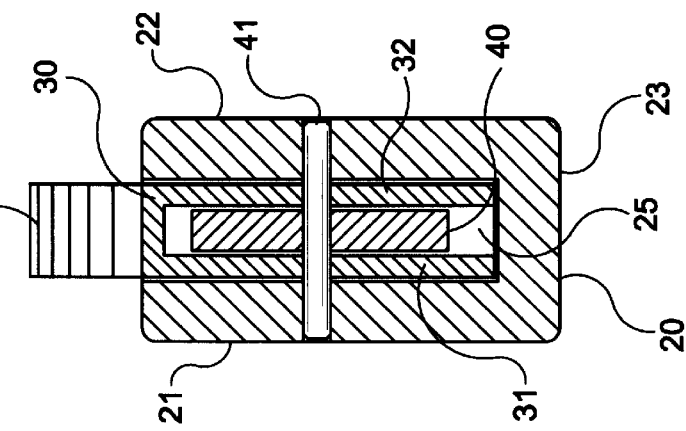

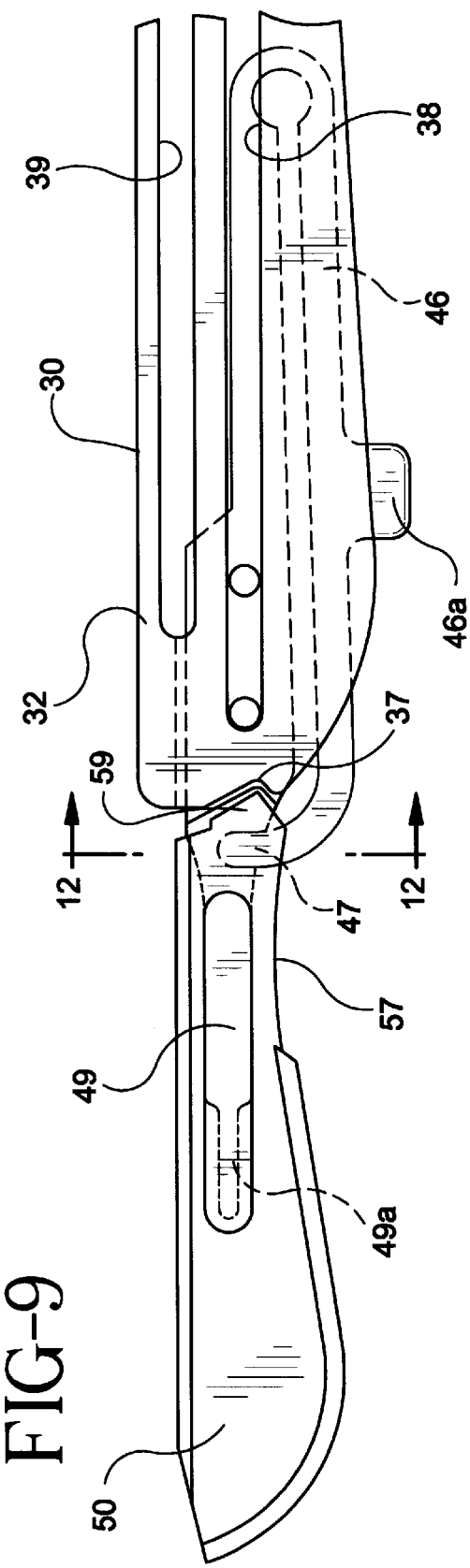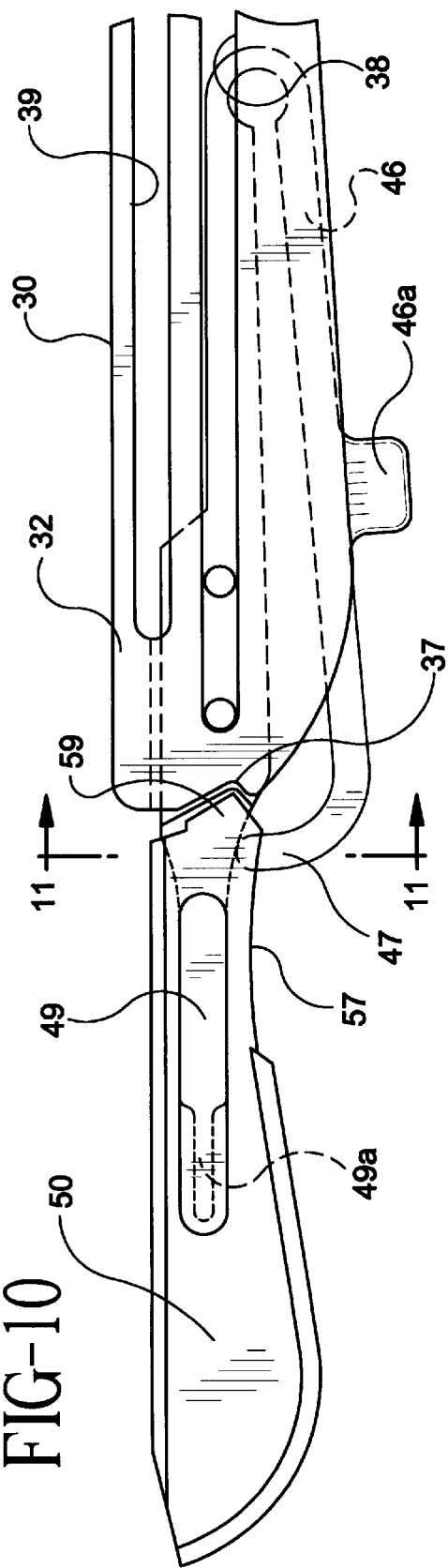

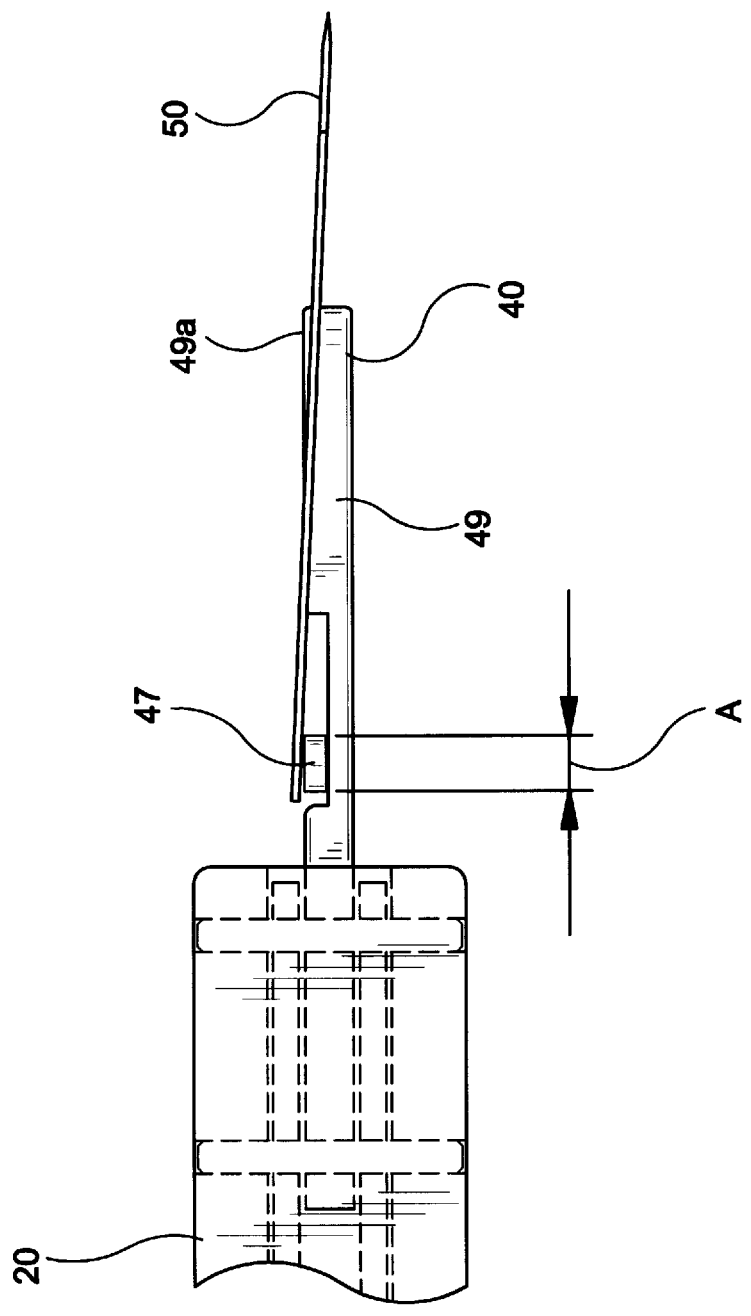

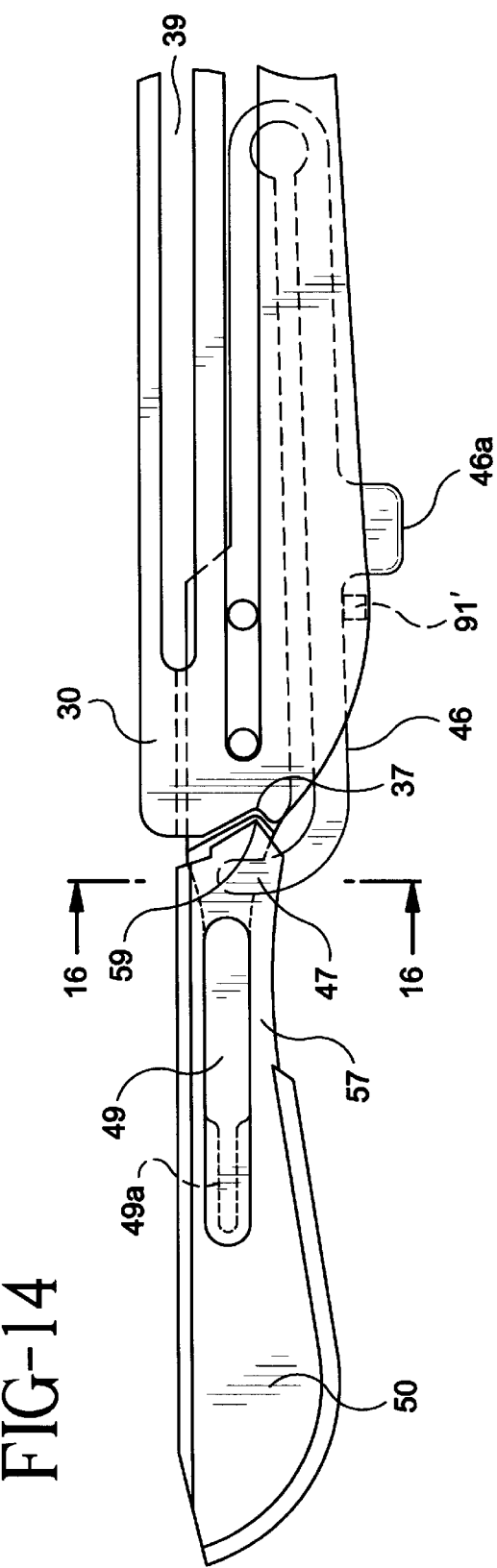
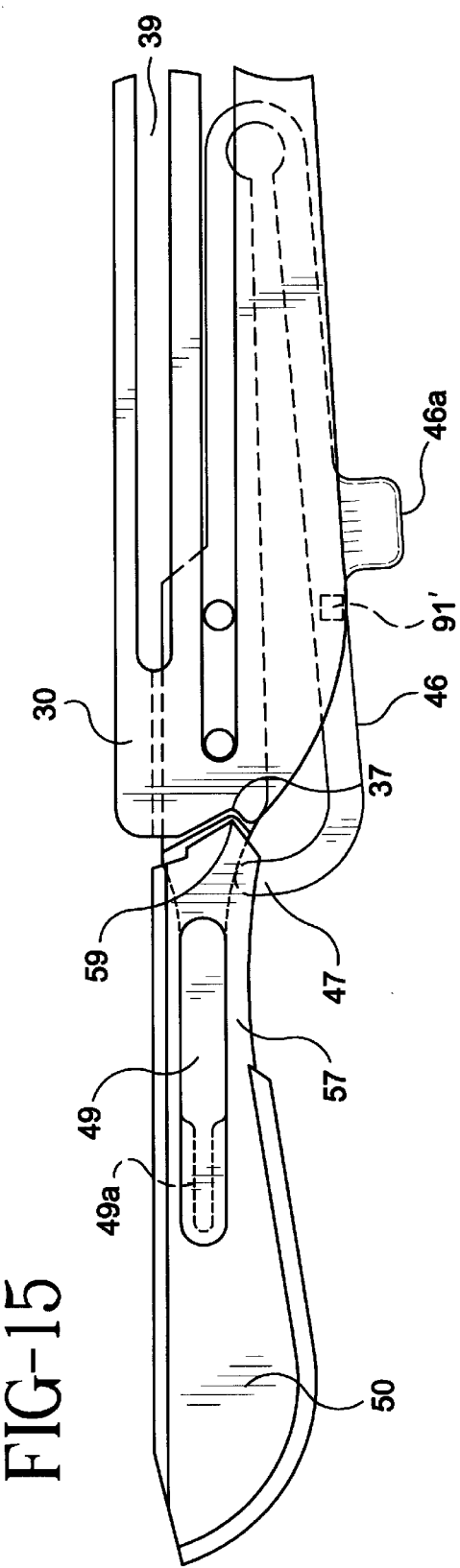

GUARDED SURGICAL SCALPEL WITH SCALPEL BLADE REMOVER

This application is a continuation-in-part of application Ser. No. 08/379,245 filed Jan. 27, 1995, now U.S. Pat. No. 5,752,968, that is a continuation-in-part of application Ser. No. 08/328,996 filed Oct. 25, 1994 that issued as U.S. Pat. No. 5,620,454 on Apr. 15, 1997.

BACKGROUND OF THE INVENTION

The present invention relates to a surgical scalpel and, in particular, to a surgical scalpel having a retractable blade guard to protect against inadvertent nicks or cuts during handling and especially during a surgical procedure in an operating room. In addition, this invention relates to a unique mechanism for removing the blade from the handle for disposal either during or at the end of the surgical procedure.

Scalpels are regularly used by surgeons and other health care professionals for making incisions in a patient during an operating procedure. Typically, a nurse hands the scalpel to the surgeon in a predetermined orientation so that the surgeon can grip the scalpel's handle without taking his or her eyes away from the patient. If the nurse accidentally touches the scalpel when it is on the table, does not pay close attention when picking up the scalpel or if the predetermined orientation is not closely followed when the scalpel is transferred to the surgeon, the nurse's or surgeon's hand may be cut or nicked by the blade of the scalpel. The same hazard of being cut or nicked by the blade may be encountered when the surgeon transfers the scalpel back to the nurse.

These nicks or cuts are uncomfortable and distracting. In addition, they may result in blood or body fluid exposure between the patient and the surgeon or other healthcare professionals in the operating room or elsewhere in the hospital. This may lead to the spread of infectious diseases between the patient and the healthcare professional. Concern over this situation has become especially acute because of such diseases as acquired immune deficiency syndrome, i.e. AIDS, and hepatitis.

While surgical gloves aid in reducing the chances of being cut during a surgical procedure, these gloves are not foolproof. And even when two sets of gloves are utilized, full protection is not afforded to the healthcare provider because the scalpel blade can still cut through both sets of gloves. Also, utilizing two sets of gloves reduces finger dexterity by the surgeon and thus is distracting to the surgeon and can interfere with the intended surgical procedure.

In view of the need for a surgical scalpel that can prevent or at least minimize the chances of accidental nicks or cuts during handling, numerous guarded surgical scalpels have been recently designed. Unfortunately, these designs are deficient because they are cumbersome, difficult to use, may cause unwanted shielding or exposure of the scalpel blade prior to the need for such shielding or exposure or may require considerable attention by the user to shield or expose the blade. In addition, these prior designs are deficient because they do not provide a safe and effective way for the blade to be removed from the handle either during or after the surgical procedure. Typically the blade tang has to be grasped by the user's hand or by a clamp and pulled from the handle. This procedure is not desirable because it exposes the person attempting to remove the blade to the risk of being cut if the user's hand is used to grasp the blade tang. And even if a clamp is used, this procedure is cumbersome at best.

SUMMARY OF THE INVENTION

It is therefore an object of the invention to provide a guarded surgical scalpel that prevents or at least minimizes the chance that the healthcare professional will be nicked or cut when the guarded surgical scalpel is handled.

It is another object of this invention to provide a guarded surgical scalpel that is easy to use and that can be operated by one hand of the user.

It is yet another object of the invention to provide a guarded surgical scalpel that will not allow the blade to be shielded or exposed prior to the need to do so.

It is still another object of this invention to provide a guarded surgical scalpel that can be used without the need for the user to observe the movement of the guard or to place undue attention to its operation.

It is still a further object of this invention to provide a guarded surgical scalpel that allows for the safe and effective removal of the blade from the handle after use.

This invention comprises a guarded surgical scalpel including a handle, a blade connected to the handle, and a guard telescopically mounted within the handle for sliding movement between a retracted position in which the blade is exposed for use and an extended position for covering the sharp cutting edge of the blade. A stop is provided between the guard and the handle for limiting the sliding movement of the guard within the handle. The stop preferably includes at least one pin mounted on the handle transversely thereof and received within a closed longitudinal slot formed in at least one of the side walls of the guard. A unique detent mechanism is provided between the guard and the handle for defining the extended position and the retracted position of the guard on the handle. The detent mechanism comprises a slot with upturned ends formed in at least one sidewall of the handle and a movable top wall formed in the guard to which a pin is connected or which has a radially extending flange formed therein. This pin or flange engages and rides in the slot formed in the handle. The top wall of the guard, and thus the pin or flange, are biased upwardly so that the pin or flange is captured in the upturned ends of the slot to prevent longitudinal movement of the guard by the application of only a longitudinal force to the guard by the user. The user, however, can move the guard by simply depressing the top wall of the guard to move the pin or flange out of engagement with the upturned ends of the slot.

The distal end of one sidewall of the guard is formed with a notch that complements a notch formed in the proximal end of the tang of the blade. By merely aligning the notch on the sidewall of the guard with the notch on the blade tang, forward movement of the guard will force the blade off of the handle. Alignment between the notch on the sidewall of the guard and the notch on the blade tang is provided by a movable lifter wedge on the blade carrier. This lifter wedge can be urged between the blade tang and the blade carrier to lift the blade tang away from the blade carrier.

DESCRIPTION OF THE DRAWINGS

The above and other objects and advantages of this invention will be apparent upon consideration of the following drawings and detailed description. The preferred embodiments of the present invention are illustrated in the appended drawings in which like reference numerals refer to like elements and in which:

FIG. 1 is a perspective view of the guarded surgical scalpel of the present invention with the guard in a retracted position to expose the blade;

FIG. 2 is a perspective view of the guarded surgical scalpel of the present invention with the guard in a partially extended position and with the guard shown in phantom in the fully extended position;

FIG. 3 is a cross-sectional view of the guarded surgical scalpel of the present invention taken along line 3—3 of FIG. 1;

FIG. 4 is a cross-sectional view of the guarded surgical scalpel of the present invention taken along line 4—4 of FIG. 1;

FIG. 9 is a side elevation view of a portion of the present invention with the lifter wedge advanced between the blade and the blade carrier;

FIG. 10 is a side elevation view of a portion of the present invention with the lifter wedge in its unbiased condition;

FIG. 13 is a top plan view of a portion of the guarded surgical scalpel of the present invention shown in FIG. 9;

FIG. 14 is a side elevation view similar to FIG. 9 but with a second embodiment of the detent mechanism for holding the lifter wedge between the blade and the blade carrier;

FIG. 15 is a side elevation view similar to FIG. 10 but showing the second embodiment of the detent mechanism for holding the lifter wedge between the blade and the blade carrier.

DETAILED DESCRIPTION OF THE INVENTION

Figure 5:
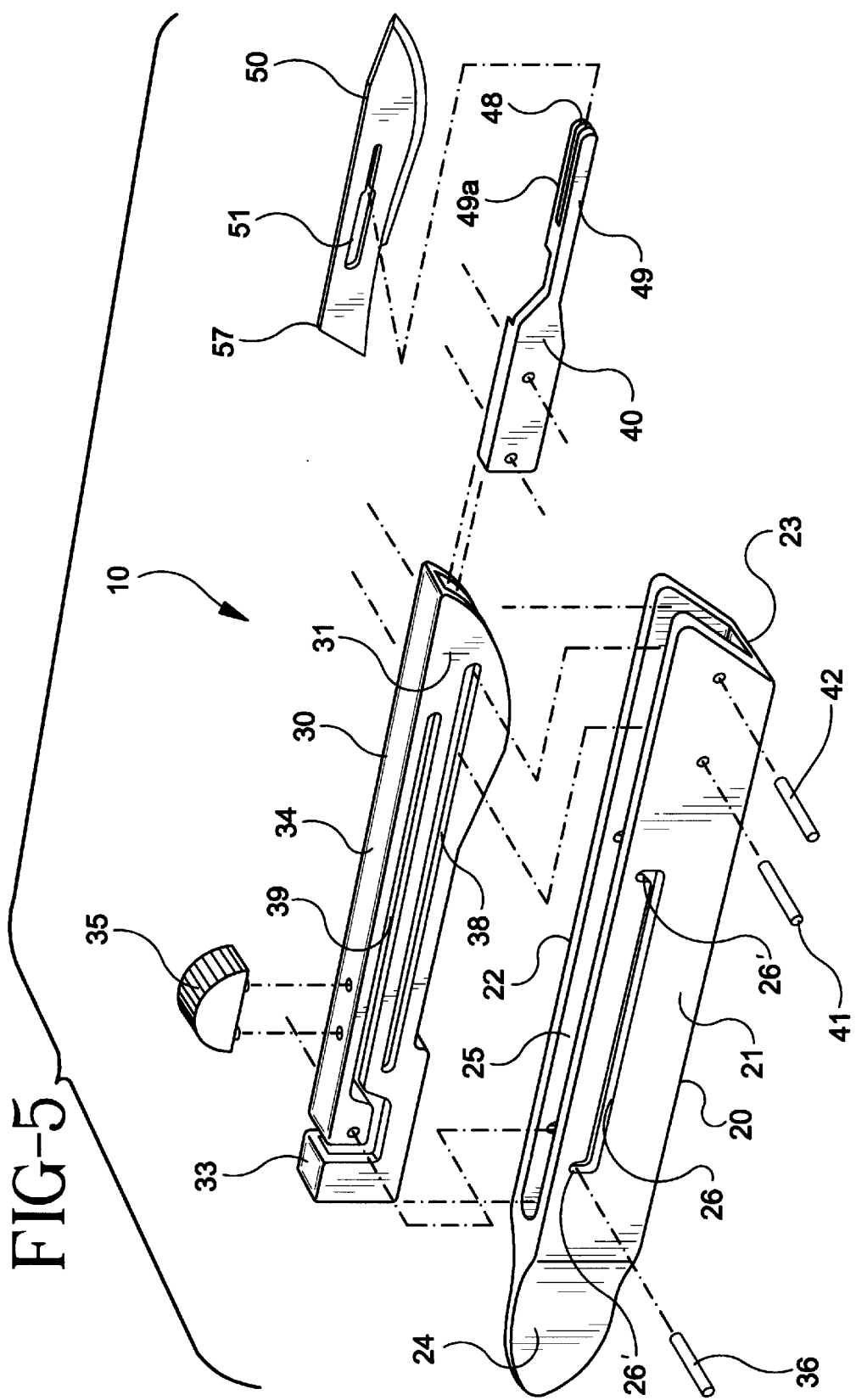
FIG. 5 is an exploded perspective view of the guarded surgical scalpel of the present invention.

The guarded surgical scalpel 10 of the present invention includes a handle 20 having a guard 30 telescopically received within handle 20 for longitudinal sliding movement in handle 20. A blade carrier 40 is mounted on the distal end of handle 20 to allow a blade 50 to be fixedly secured to the distal end of handle 20. Blade carrier 40 is mounted to handle 20 by two transverse pins 41, 42 that extend across the width of handle 20. Pins 41, 42 can be bonded to blade carrier 40 and handle 20 by any conventional means such as orbital riveting, chemical adhesive, ultrasonic bonding, welding or brazing.

Handle 20 has two parallel side walls 21, 22, a bottom wall 23 and a closed proximal end 24. This configuration for handle 20 defines a cavity 25 therein. Proximal end 24 of handle 20 is tapered to a thin portion to provide a blunt dissection tool that can be used during the operating procedure. Side wall 21 of handle 20 preferably defines a slot 26 that is aligned with a slot (not shown) formed in opposing side wall 22. Each slot is generally parallel to the longitudinal axis of handle 20. In addition, the ends of each slot have upturned portions 26' extending away from the main portion of the slot. It is to be noted that the configuration of slot 26 is a mirror image of the configuration of the slot formed in side wall 22. Preferably handle 20 is formed from 410 stainless steel. However, 303 stainless steel or 420 stainless steel could also be used. In order to have a comfortable and functional product, handle 20 preferably has an overall length of about 4.180 inches, an overall width of about 0.310 inches and an overall height of about 0.520 inches. Preferably the slots each have an overall length of about 1.875 inches.

Guard 30 preferably has two parallel side walls 31, 32 which are connected by a proximal top wall 33 and a distal top wall 34. Preferably side walls 31, 32 have a shape similar to that of a standard surgical scalpel blade. Using this shape for side walls 31, 32 helps the user of guarded surgical scalpel 10 intuitively to understand how to hold and use guarded surgical scalpel 10. Preferably guard 30 is formed from 410 stainless steel but 303 stainless steel or 420 stainless steel, can also be used. Because guard 30 slides past blade carrier 40 and handle 20, guard 30 is preferably treated by titanium nitride or chromium nitride vapor deposition. This treatment hardens the surface of guard 30 and prevents galling thereby ensuring smooth operation of guarded surgical scalpel 10 over its useful life.

Figure 8:
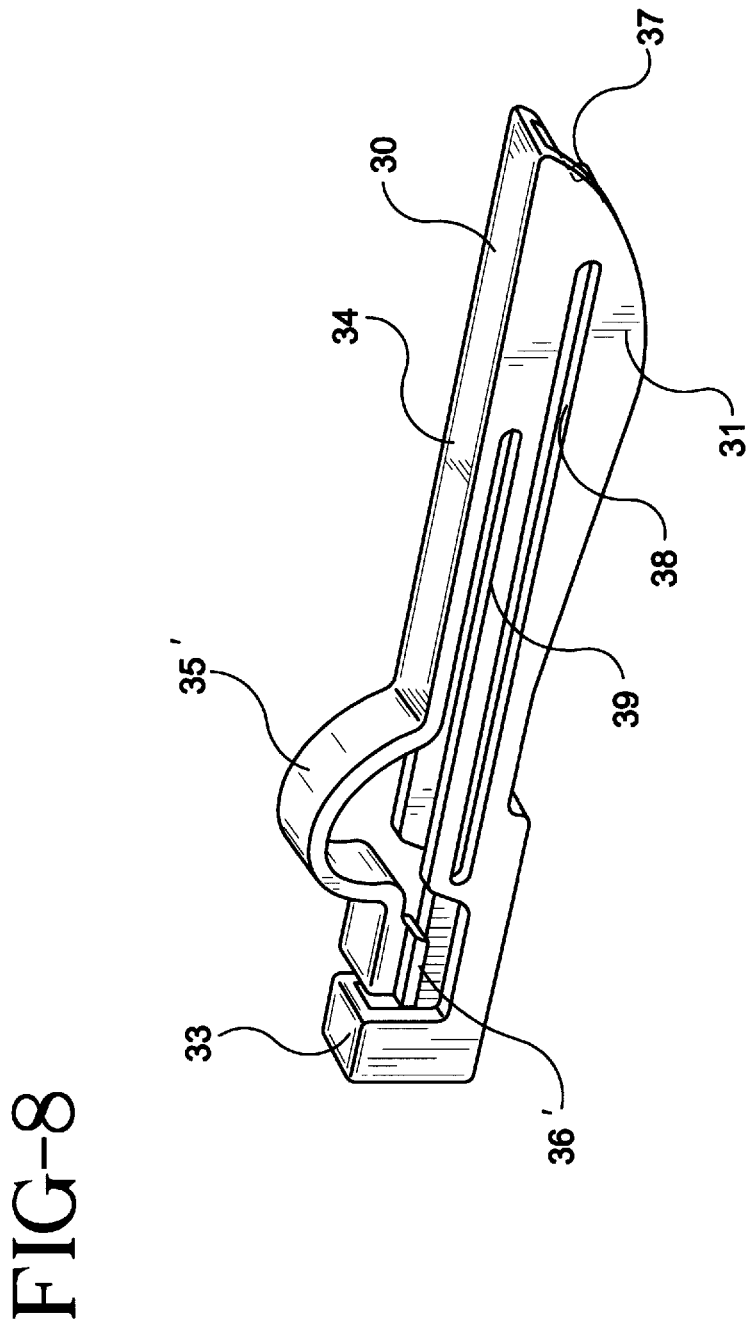
FIG. 8 is a perspective view of another embodiment of the guard used in the guarded surgical scalpel of the present invention.
Figure 12:
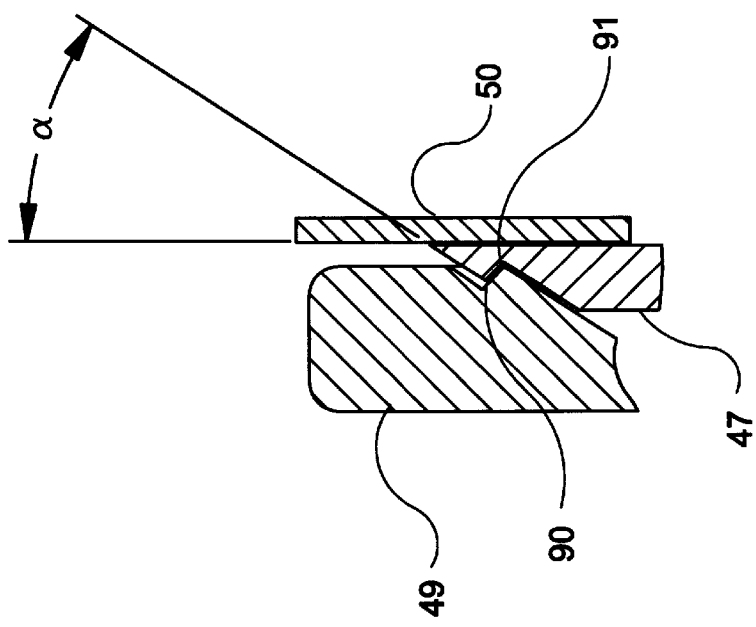
FIG. 12 is cross-sectional view of the embodiment of the guarded surgical scalpel of the present invention taken along line 12—12 of FIG. 9.
Figure 11:
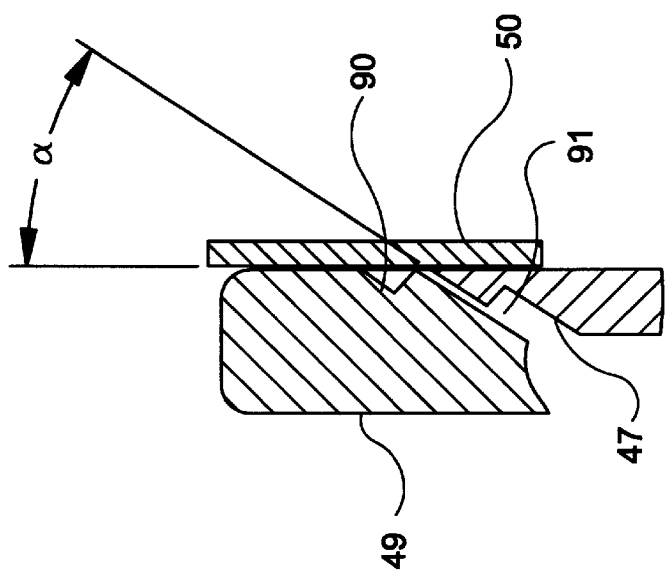
FIG. 11 is a cross-sectional view of the guarded surgical scalpel of the present invention taken along line 11—11 of FIG. 10.

Side wall 31 defines an upper slot 39 adjacent to distal top wall 34 along substantially the entire length of side wall 31 except for the most distal portion thereof. Side wall 32 also has an upper slot formed therein (not shown) which is aligned with slot 39. It is to be understood that the configuration of slot 39 is a mirror image of the configuration of the upper slot formed in side wall 32. This allows distal top wall 34 to be flexed downwardly in a cantilevered fashion. Depressible distal top wall 34 carries a detent button 35 to facilitate downward flexing of distal top wall 34. Alternatively, distal top wall 34 can be formed with a bump 35' therein to facilitate downward flexing of distal top wall 34. See FIG. 8. A detent pin 36 is located adjacent to the proximal end of distal top wall 34 and may be bonded thereto by press fit, welding or chemical adhesive. Alternatively and preferably, a radially extending flange 36' is formed along the proximal end of distal top wall 34. See FIG. 8. By using radially extending flange 36' formed in distal top wall 34, a separate element, i.e. pin 36, does not have to be secured to distal top wall 34. This facilitates the manufacturing of guarded surgical scalpel 10. It is to be understood that detent pin 36 and radially extending flange 36' preferably extend radially from both sides of distal top wall 34.

Guard 30 is preferably mounted in cavity 25 of handle 20 for telescopic movement therein and should be dimensioned to allow a tight yet movable fit therein. In order to allow such movement by guard 30, blade carrier 40 is centrally mounted across the distal open end of handle 20 to allow a clearance on either side of blade carrier 40 for side walls 31, 32 of guard 30. This arrangement requires a lower slot 38 to be formed in side wall 31. Side wall 32 also has a lower slot formed therein (not shown) which is aligned with slot 38. It is to be understood that the configuration of lower slot 38 is a mirror image of the configuration of the lower slot formed in side wall 32. Pins 41, 42 engage the ends of the lower slots formed in side walls 31, 32 to limit the sliding movement of guard 30 relative to handle 20. By placing guard 30 within cavity 25, detent pin 36, or radially extending flange 36', extends into and rides in the slots formed in side walls 21, 22 of handle 20 and is biased into the upturned portions provided at the ends of these slots when guard 30 is in the fully extended or the fully retracted position. The length of these slots formed in side walls 21, 22 of handle 20 is equal to the amount of travel of guard 30.

When detent pin 36, or radially extending flange 36', is located in the upturned portions at the ends of the slots formed in side walls 21, 22 of handle 20, guard 30 is temporarily locked in the extended or retracted position. If the user were to inadvertently apply a longitudinal force to guard 30, detent button 35 or bump 35' when guard 30 was in one of these positions, guard 30 would not move. In order to move guard 30, a downward force must be applied to distal top wall 34, detent button 35 or bump 35' to move pin 36, or radially extending flange 36', out of engagement with the upturned portions at the ends of the slots formed in side walls 21, 22 of handle 20. Thus, the chance that the user would inadvertently shield or expose blade 50 prior to the need to do so is minimized. In addition, because of the upward bias of distal top wall 34, and thus detent pin 36, or a radially extending flange 36', the user will automatically know when guard 30 has been moved completely to the extended or retracted position by an audible "click" when pin 36, or radially extending flange 36', engages one of the upturned portions at the ends of the slots formed in side walls 21, 22 of handle 20.

In order to allow the user to flex distal top wall 34 downwardly with a comfortable force, the distal portion of the upper slots formed in side walls 31, 32 of guard 30 should begin about 1.1 inches from the distal end of guard 30 when guard 30 is formed from 410 stainless steel. If guard 30 is formed from a softer material such as plastic this distance could be greater. In addition, these upper slots should have a height of about 0.065 inches. These dimensions allow sufficient downward movement of detent pin 36, or radially extending flange 36', so it can be moved out of engagement from the upturned portions of the slots formed in side walls 21, 22 of handle 20.

Figure 6:
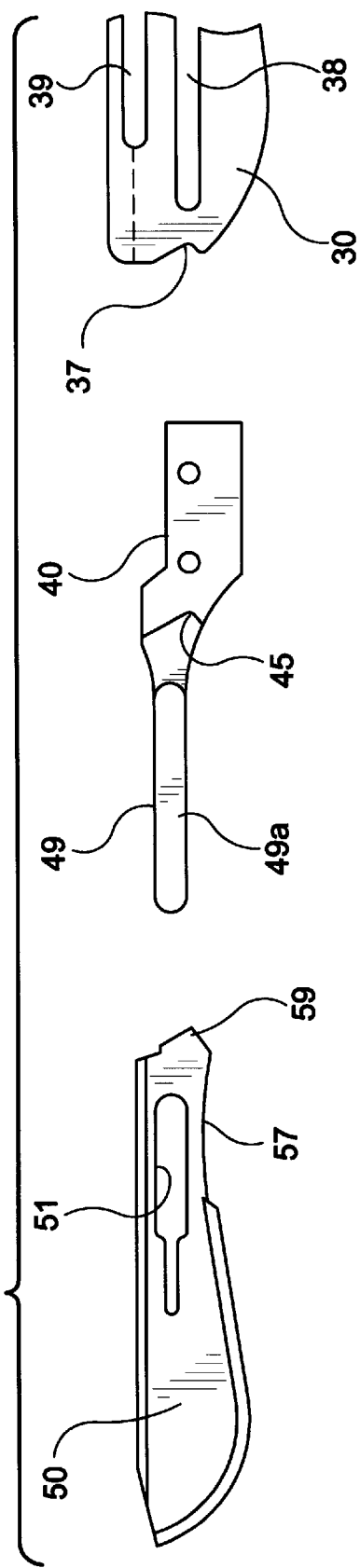
FIG. 6 is an exploded side elevation view showing a portion of the guarded surgical scalpel of the present invention.
Figure 7:
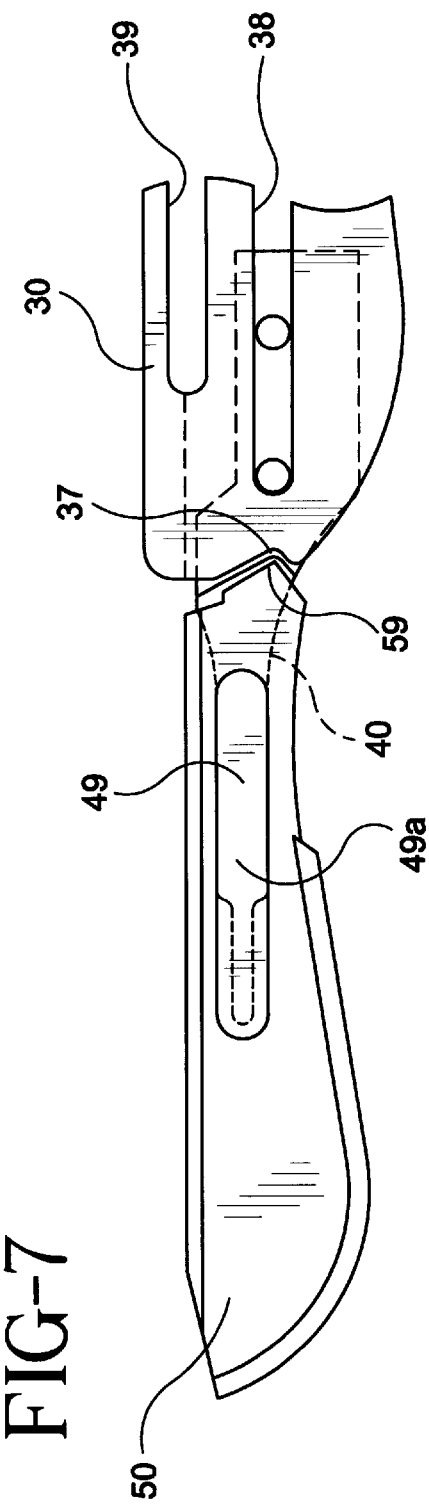
FIG. 7 is a side elevation view showing a portion of the guarded surgical scalpel of the present invention with the guard in a retracted position to expose the blade and with the notch on the blade aligned with the notch on the guard.

Blade carrier 40 extends forwardly of handle 20 in a cleat 49 and has a laterally-extending longitudinal rib 49a provided with an external groove 48. Blade carrier 40 is preferably formed from 410 stainless steel. However, 303 stainless steel or 420 stainless steel, could also be used. Blade 50 has a longitudinal slot 51 which cooperates with groove 48 and rib 49a to mount blade 50 on blade carrier 40, thereby mounting blade 50 on handle 20. Blade 50 is relatively thin and very sharp and is "snapped" over rib 49a on blade carrier 40. As shown in FIGS. 6 and 7, blade carrier 40 may include a notch 45 formed therein that mates with another notch 59 formed in the blade tang 57. In addition, sidewall 32 of guard 30 can have a notch 37 that matches notch 45. This configuration may be used, if desired, to ensure that only the appropriate blades are used with guarded surgical scalpel 10. In addition, this configuration provides another benefit. By slightly lifting blade tang 57, notch 37 of guard 30 can engage notch 59. Once these notches are engaged, guard 30 can be advanced distally to force blade 50 from blade carrier 40. If desired, sidewall 31 could also have a notch that matches notch 35.

The embodiments of the guarded surgical scalpel of this invention shown in FIGS. 9 through 16 provide simple mechanisms to lift blade tang 57 to allow notch 37 to engage notch 59. A cantilever spring arm 46 is formed in blade carrier 40. The distal end of cantilever spring arm 46 includes a wedge shaped portion 47 that aligns with the interface between blade cleat 49 and blade 50. Preferably wedge 47 is formed with an angle $\alpha$ of about 30 degrees and dimension A of between about 0.125 inches and 0.313 inches. Spring arm 46 and wedge 47 are arranged on blade carrier 40 so that the tip of wedge 47 extends to cleat 49 in the unbiased condition. See FIG. 10. In this way, the tip of wedge 47 is already in the interface between cleat 49 and blade tang 57. By moving cantilever spring arm 46 toward this interface by pushing button 46a, wedge 47 causes blade tang 57 to move away from cleat 49 to facilitate engagement between blade notch 59 and guard notch 37. This arrangement of spring arm 46 and wedge 47 allows the healthcare worker to remove blade 50 without touching any part of blade 50 by simply advancing guard 30 distally. Preferably, cantilever spring arm 46 is about 1 inch long and about 0.125 inches thick. It is connected to blade carrier 40 via a flexural hinge to facilitate movement of wedge 47 toward the interface between cleat 49 and blade tang 57.

Wedge 47 and blade carrier 40 are configured to provide a detent mechanism that holds wedge 47 in the interface between blade cleat 49 and blade tang 57. Specifically, blade cleat 49 is formed with a shoulder 90 that engages the shoulder 91 formed between wedge 47 and spring arm 46. In this way, the user need not constantly squeeze spring arm 46 to raise blade tang 57. Instead, shoulders 90 and 91 hold wedge 47 in the interface between blade cleat 49 and blade tang 57 while blade 50 remains on blade carrier 40. See FIG. 12. While blade 50 is connected to blade cleat 49, blade 50 serves to force shoulders 90 and 91 into engagement with one another. Once blade 50 has been removed from blade carrier 40, shoulders 90 and 91 disengage to allow spring arm 46 to return to its unbiased position.

Figure 16:
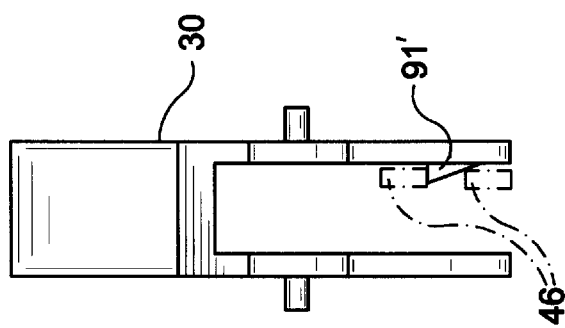
FIG. 16 is an end elevation view of the guard taken along line 16—16 of FIG. 14 showing the second embodiment of the detent mechanism for holding the lifter wedge between the blade and the blade carrier with the spring arm connected to the lifter wedge shown in phantom in both the biased and unbiased position.

In another embodiment shown in FIGS. 14–16, the detent mechanism merely comprises a shoulder 91' that holds the bottom of spring arm 46 in the biased position so wedge 47 is in the interface between blade cleat 49 and blade tang 57. See FIG. 14. Once guard 30 is advanced to eject blade 50 from blade carrier 40, shoulder 91' no longer engages spring arm 46 because shoulder 91' is extended past spring arm 46. This allows spring arm 46 to be returned to its unbiased position. See FIG. 15 where spring arm 46 is in its unbiased position and guard 30 has been retracted into handle 20. Thus a new blade can be subsequently installed on blade carrier 40.

Thus, it is seen that a guarded surgical scalpel is provided that prevents, or at least minimizes, the chances for nicks or cuts during handling, that is easy to use and can be operated by one hand of the user, that will not allow the blade to be shielded or exposed prior to the need to do so, that can be used without the need for the user to observe the movement of the guard or to place undue attention to its operation and that provides a simple, safe and effective way to remove the blade from the handle.

We claim:

1. A method for removing a blade, having a proximal end, from a guarded surgical scalpel having a guard with a distal end and a blade carrier for carrying the blade, comprising:

lifting the proximal end of the blade from the blade carrier;

engaging the proximal end of the blade with the distal end of the guard; and moving the guard in a distal direction to force the blade from the guarded surgical scalpel, wherein the guarded surgical scalpel includes a wedge operably connected to the blade carrier and movable from an unbiased position to a biased position between the blade carrier and the blade for lifting the proximal end of the blade from the blade carrier and further comprising the step of maintaining the wedge in the biased position until the guard is moved in the distal direction.

2. The method of claim 1 wherein the proximal end of the blade defines a notch and the distal end of the guard defines a notch that is complementary to the notch in the proximal end of the blade so the blade notch is engaged with the guard notch during the engaging step.

3. The method of claim 1 further comprising the step of moving the wedge to the unbiased position after the guard is moved in the distal direction.

4. The method of claim 3 wherein the proximal end of the blade defines a notch and the distal end of the guard defines a notch that is complementary to the notch in the proximal end of the blade so the blade notch is engaged with the guard notch during the engaging step.

5. A guarded surgical scalpel handle for holding a blade, comprising:
   a handle body a guard telescopically received within the handle body for longitudinal movement with respect to the handle body; and
   a blade carrier extending from the distal end of the handle body, said blade carrier having a portion adapted to mount a blade, said blade carrier further comprising a cantilever spring arm disposed to move toward and away from the portion of the blade carrier.

6. The guarded surgical scalpel handle of claim 5 further comprising a blade defining a plane mounted to blade carrier such that movement of the cantilever spring arm toward the blade carrier in the plane of the blade urges the blade away from the blade carrier.

7. The guarded surgical scalpel handle of claim 6 wherein the blade includes a proximal end with a notch formed therein and the guard includes a distal end with a complementary notch formed therein.

8. The guarded surgical scalpel handle of claim 5 further comprising a wedge at the distal end of the cantilever spring arm.

9. The guarded surgical scalpel handle of claim 8 wherein the wedge defines a first shoulder with the cantilever spring arm and the blade carrier defines a second shoulder for engagement with the first shoulder.

10. The guarded surgical scalpel handle of claim 9 further comprising a blade defining a plane mounted to the blade carrier such that movement of the spring arm in the plane of the blade toward the blade carrier urges the blade away from the blade carrier.

11. The guarded surgical scalpel handle of claim 10 wherein the blade includes a proximal end with a notch formed therein and the guard includes a distal end with a complementary notch formed therein.

12. The guarded surgical scalpel handle of claim 8 wherein the guard includes a shoulder to engage the cantilever spring arm to hold the wedge adjacent to the blade carrier.

13. The guarded surgical scalpel handle of claim 12 further comprising a blade defining a plane mounted to the blade carrier such that movement of the cantilever spring arm toward the blade carrier in the plane of the blade urges the blade away from the blade carrier.

14. The guarded surgical scalpel handle of claim 13 wherein the blade includes a proximal end with a notch formed therein and the guard includes a distal end with a complementary notch formed therein.

* * * * *